(12) United States Patent
de Juan, Jr. et al.

(10) Patent No.: US 6,969,384 B2
(45) Date of Patent: Nov. 29, 2005

(54) SURGICAL DEVICES AND METHODS OF USE THEREOF FOR ENHANCED TACTILE PERCEPTION

(75) Inventors: Eugene de Juan, Jr., Baltimore, MD (US); Patrick S. Jensen, Issaquah, WA (US)

(73) Assignee: The Johns Hopkins University, Baltimore, MD (US)

( * ) Notice: Subject to any disclaimer, the term of this patent is extended or adjusted under 35 U.S.C. 154(b) by 289 days.

(21) Appl. No.: 09/756,649

(22) Filed: Jan. 3, 2001

(65) Prior Publication Data

US 2001/0025150 A1 Sep. 27, 2001

Related U.S. Application Data

(60) Provisional application No. 60/174,260, filed on Jan. 3, 2000.

(51) Int. Cl.[7] .............................................. A61B 17/00
(52) U.S. Cl. .......................................... 606/1; 600/587
(58) Field of Search .............................. 606/1, 38, 131; 600/587, 424, 101; 607/102

(56) References Cited

U.S. PATENT DOCUMENTS

| | | | | |
|---|---|---|---|---|
| 4,841,987 A | * | 6/1989 | Brown et al. ................ | 128/777 |
| 4,951,671 A | * | 8/1990 | Coan ........................... | 128/652 |
| 5,047,046 A | * | 9/1991 | Bodoia ........................ | 606/205 |
| 5,188,111 A | | 2/1993 | Yates et al. .................. | 128/657 |
| 5,221,280 A | * | 6/1993 | Gross et al. .................. | 606/36 |
| 5,411,511 A | * | 5/1995 | Hall ............................. | 606/166 |
| 5,437,657 A | * | 8/1995 | Epstein ......................... | 606/4 |
| 5,611,805 A | * | 3/1997 | Hall ............................. | 606/166 |
| 5,649,934 A | * | 7/1997 | Smeltzer III et al. ........ | 606/122 |
| 5,728,044 A | * | 3/1998 | Shan ........................... | 600/145 |
| 5,746,748 A | * | 5/1998 | Steinberg et al. ........... | 606/118 |
| 5,771,902 A | * | 6/1998 | Lee et al. .................... | 128/897 |
| 5,836,894 A | * | 11/1998 | Sarvazyan ................... | 600/587 |
| 5,928,158 A | * | 7/1999 | Aristides ..................... | 600/547 |
| 6,033,409 A | * | 3/2000 | Allotta ........................ | 606/80 |
| 2001/0004700 A1 | * | 6/2001 | Honeycutt et al. .......... | 606/159 |

FOREIGN PATENT DOCUMENTS

| | | | |
|---|---|---|---|
| DE | 4206126 | * | 9/1993 |
| EP | 349443 | * | 1/1990 |
| JP | 6-142031 | * | 5/1990 |
| JP | 7-171425 | * | 7/1995 |
| JP | 9-98978 | * | 4/1997 |
| RU | 733670 | * | 5/1980 |
| WO | WO98/43693 | | 10/1998 |

OTHER PUBLICATIONS

Tanimoto et al, "Micro Force Sensor for Intravascular Neurosurgery and In Vivo Experiment," Proc. MEMS 98, IEEE 11th Intl Workshop Micro Electro Mech Systems, Jan. 25–29, 1998.*

Sukthankar, SM et al, "Towards Force Feedback in Laprascopic Surgical Tools," Proc of 16th Intl Conf of IEEE Engr in Med and Biol Soc., p. 1041–2, vol. 2, 1994.*

Nissan, M., et al, "Strain Gauged Haemostatic Forceps for Clinical & Experimental Use," Med. & Biol. Engr & Computing, vol. 26, no. 4, pp. 448–50, Jul. 1988.*

(Continued)

*Primary Examiner*—John A. Jeffery
(74) *Attorney, Agent, or Firm*—Peter F. Corless; Edwards & Angell, LLP (57) ABSTRACT

Featured are surgical devices that provide enhanced perceptual feedback to a medical practitioner in the form of e.g. tactile sensations or auditory feedback, and methods of use of the devices. The devices and methods of the present invention are particularly suitable for microsurgery applications including ophthalmic or neurosurgical procedures. Use of the present devices and methods will enhance user feedback, allowing for improved perception, thereby increasing performance, speed, and accuracy of surgical procedures.

48 Claims, 8 Drawing Sheets

OTHER PUBLICATIONS

Dargahi, J., et al, "A Micro–Strain Gauge Endoscopic Tactile Sensor Using Two Sensing Elements for Tissue Manipulation," Proc of SPIE, Intl Soc Opt. Engr, Conf. Sensor Fusion, Apr. 25–28, 2000.*

Waturu Miyoshi et al., "Development of Force Sensing Injector", Nippon Kikai Gakkai Joho, Seimitsu Kiki Bumon Koenkai Koen Ronbunshu (1999) vol. 1999, pp. 78–80.*

* cited by examiner

SURGICAL DEVICES AND METHODS OF USE THEREOF FOR ENHANCED TACTILE PERCEPTION

This application claims the benefit of U.S. Provisional Application Ser. No. 60/174,260 filed Jan. 3, 2000, the teaching of which is incorporated herein by reference.

FIELD OF THE INVENTION

The present invention relates to improved surgical devices and methods of use thereof. More particularly, the present invention relates to surgical devices and methods that provide enhanced perceptual feedback to a medical practitioner e.g. in the form of tactile sensations or auditory feedback. The devices and methods of the invention are particularly suitable for microsurgery applications, especially ophthalmic and/or neurosurgical procedures.

BACKGROUND OF THE INVENTION

Microsurgery involves the manipulation of delicate membranes and vessels with a required accuracy often on the order of tens of microns, a scale at or near the limit of human positional ability [C. N. Riviere, R. S. Rader, and P. K. Khosla, "Characterisitcs of hand motion of eye surgeons," presented at IEEE Engineering in Medicine and Biology Society, Chicago, 1997; M. U. Humayun, R. S. Rader, D. J. Pieramici, et al., "Quantitative measurement of the effects of caffeine and propranolol on surgeon hand tremor.," *Arch Ophthalmol*, vol. 115, pp. 371–374, 1997.] Forces imposed by the tissue on the surgical tool during these manipulations are exceedingly small. Research indicates that tactile sensation tools interacting with an environment is an important factor in task performance. For example, vitreoretinal surgeons cannot "feel" the majority of interactions between the surgical instruments they are holding and the retinal tissue being manipulated [Gupta, P. and Jensen, P. S. "Surgical Forces and Tactile Perception During Retinal Microsurgery", *Second International Conference on Medical Image Computing and Computer-Assisted Intervention (MICCAI)*, Cambridge England, Sep. 20–22, 1999.]. In other words, the forces being imparted on the retina by the medical practitioner through the use of a surgical tool are typically too small to be perceived by the medical practitioner's fingertips. As a result, the medical practitioner must rely primarily on visual feedback to position the instruments and to manipulate the retinal tissue.

Although the view through the operating microscope is quite good, prior studies have demonstrated that a lack of tactile and haptic sensation while performing manual manipulation tasks leads to both increased errors and increased task completion times. For example, it was demonstrated by Howe [Howe, R. D., et. al. "Tactile display of vibratory information in teleoperation and virtual environments." *Presence*, 1995 4(4):387–402.] that manually inserting a peg into a hole using only visual information, although possible, took up to ten times longer to complete and had significantly greater positioning error than when tactile sensation was provided. Studies have also shown that a combination of at least two agreeing perceptual inputs significantly improves task performance [Sage, G. H. "Introduction to Motor Behavior: A neurophysical Approach". Addison-Wesley Publishing: Reading, Mass., 1984.]. In addition, the visual feedback pathway is slow compared to both auditory and mechanical responses, thus making secondary perceptual input useful during manual manipulations [Patkin, M. "Ergonomics applied to the practice of microsurgery", Aust NZ J Surg, 1977, 47(3):320–329.]. We therefore know that A) many interactions between the surgical tool and the tissues in particular applications are too small to be felt by the medical practitioner, B) performing manual tasks without a sense of touch increases positional errors and task completion times, and C) incorporating multi-sensory information (i.e. sight+touch or sight+auditory) significantly increases manual task performance. Since relying on visual feedback alone has been shown to both increase the length of manual manipulation tasks and reduce task accuracy, augmenting tactile perception during microsurgery can potentially reduce surgical execution time while increasing surgical precision.

It would thus be desirable to have improved surgical devices that provide a medical practitioner with enhanced perceptual feedback during the manipulation of tissue in the form of tactile sensations and/or auditory feedback, thereby improving the performance, accuracy and speed of the surgical procedure.

SUMMARY OF THE INVENTION

We have now discovered new surgical devices and methods for use thereof that can overcome the prior limited tactile and haptic sensations available to the medical practitioner.

More particularly, instruments of the invention are capable of providing a sensory input back to the medical practitioner (e.g. surgeon performing microsurgery). For instance, a tactile, auditory or other input can be provided to the medical practitioner of interaction of the device with the patient, e.g. contact and manipulation of tissue with the device. Tactile and auditory indication to the medical practitioner are particularly preferred.

Preferred devices of the invention comprise a sensor element that is capable of detecting interaction of the device with the environment. Information, particularly non-visual information relating to the device interaction then can be communicated in real-time or otherwise to a user of the device, e.g. as tactile or auditory information. The device suitably detects physical interaction, electrical properties or spatial relation of the device. Both static and dynamic motion of the device is suitably detected and communicated to a device user. The information relating to forces imparted on the device preferably are amplified and then communicated to a user of the device to facilitate perception of modest motion or other interactions of the device.

The sensor element of the device suitably transmits an electrical signal in response to forces imparted on the device, particularly forces imparted on the device distal end. The sensor element can be a relatively wide variety of configurations, including e.g. located at the device distal end as well as along the length of the device.

Particular preferred devices of the invention include a sensor element that can generate a electrical signal based on forces imparted on the device, which forces may be static or dynamic; an electronic controller that can generate an output signal based on the electrical signal; and an output transducer that receives the output signal, thereby producing a proportional sensory signal. The device may further comprise an energy conducting apparatus that can transmit the output signal from the electronic controller to output transducer. The device also may further include an apparatus can transmit electric signals between the sensor element and the electronic controller. Suitably the device comprises a power source, e.g. a battery, or operated by external power source such as a supplied electric current.

The invention includes a variety of medical instruments. Generally preferred are grasping or other manipulation devices such as picks and the like. Herein, a surgical instrument may be referred to without limitation as a "tactile pick" or "pick," a "surgical device," "surgical pick," "device," or "instrument."

Preferred instruments of the invention comprise a surgical pick, dissector, retractor, grasper, or other manipulation element that comprises a sensitive sensor element, typically at a distal portion (i.e. an end opposite from that used by a medical practitioner). The sensor element can communicate sensory indication to the medical practitioner, preferably at a threshold what may be felt by the medical practitioner. In one preferred design, the instrument comprises an elongate or shaft member and a sensory link between the instrument distal end and the medical practitioner's hand at the device proximal end. Preferably, interactions between the tool and the tissue normally below the threshold of what may be felt by the medical practitioner are detected by the sensor, amplified and then presented to the medical practitioner through an output (e.g. output transducer) which yields amplified signals.

Thus, surgical instruments of the invention provide a medical practitioner with enhanced perceptual information. As mentioned, the perceptual information may take the form of e.g. either enhanced tactile sensation or an auditory tone correlated with the interaction of surgical tools with tissue. The surgical device is particularly suitable for ophthalmic procedures, especially retinal procedures, during which a surgeon typically relies solely on visual feedback.

Other procedures where visual feedback is a primary guide to the surgeon also are particularly suited for applications of the present invention, including a wide variety of microsurgery procures, such as a wide variety of endoscopic procedures, including laparascopic and thoracoscopic procedures.

Additionally, surgical devices of the invention are particularly suitable for neurosurgical procedures, an additional surgical situation in which a surgeon relies on visual feedback, and requires particular care and precision in procedures.

Preferably, a surgical device of the invention is sterilizable for reuse of the device, although the invention also includes single-use devices. Additionally preferable are embodiments where the device is self contained, wherein certain parts of the device are modular and disposable or reuseable.

In a preferred embodiment, the tip of the surgical device is equipped with a sensor that determines one or more of the physical properties of surgery. These properties include, but are not limited to, physical interactions between the surgical tool and the tissue (i.e. stress, strain, force, acceleration), electrical properties between the surgical tool and the tissue (i.e. impedance, magnetic flux) and/or spatial relations between the surgical tool and the tissue (i.e. contact, proximity). Information collected from the sensor is processed and delivered to the medical practitioner in a non-visual manner, preferably e.g. via an electromechanical transducer such as a tactile actuator located within the device such as the device handle held by the medical practitioner; a tactile actuator attached to another location on the medical practitioner's body (i.e. ear lobe, toe), or through an auditory device such as a speaker, headphone, earphone, etc.

A surgical device of the invention (e.g. a surgical pick) is suitably equipped with a sensor capable of detecting minute interactions between the pick and manipulated tissue (e.g. retinal tissue) normally too small to be discerned by the medical practitioner. More particularly, in a preferred design, an electronic signal from the sensor element is amplified and used to drive a sensory indication to the medical practitioner, e.g. an auditory speaker within hearing range of the medical practitioner, allowing the medical practitioner to detect such things as when the surgical tool contacts retinal tissue without having to rely purely on visual information.

In a preferred embodiment, signal from the sensor element is conditioned, filtered, isolated and amplified through an electronic controller which is connected via conducting means to the sensor element. The controller is additionally connected via conducting means to an output transducer, whereby output signal is transmitted to achieve emission of signal to the medical practitioner.

Preferred devices of the present invention may include power sources connected to the instrument such as power cord attachment for A/C power. Alternatively, the device may comprise a self-contained battery powered unit.

Devices of the invention (e.g. a tactile pick) can be identical or substantially corresponding in shape and function to a variety currently available devices, including a variety of currently existing picks available for microsurgery, particularly vitreoretinal surgery. Since the addition of the sensor to the instrument does not effect the shape of the pick or the manner in which it is used, the protocol for using the tactile pick will be the same as that for using any other surgical pick. The benefit of using the tactile pick will be the addition of sensory information corresponding to minute tool-tissue forces normally unperceptible by the medical practitioner, therby improving performance of the surgical procedure.

In a preferred embodiment, the sensor of the surgical device is a piezopolymer or piezoresistive material. The piezopolymer generates an electric signal when dynamically flexed that is proportional to the degree of flexion. The piezoresistive material generates an electric signal in response to static pressure as well as dynamic responses. The signal is subsequently isolated, amplified, filtered, processed and delivered to the medical practitioner through an output device.

In an additional preferred embodiment, the sensor of the surgical device comprises strain gauges or other suitable sensors mounted on the side of the shaft of the device, whereby the gauges detect movement of the shaft.

In a particularly preferred embodiment, a tactical signal is delivered to the medical practitioner by electromechanical device located on the body of the surgical device, or an electromechanical device held or attached directly to the medical practitioner. In another embodiment, a sensory signal (e.g. tactile or auditory) is delivered to the medical practitioner, e.g. in the case of an auditory out through an amplified speaker. In one embodiment, the output device is a small speaker glued inversely to the handle such that when the signal is delivered to speaker, the cone of the speaker remains stationary while body of speaker moves, thus providing tactile sensation. In another embodiment, the medical practitioner may hold the device in one hand and a speaker in the opposite hand so that the medical practitioner may both feel and hear the output.

By providing enhanced perceptual information to the medical practitioner during the manipulation of surgical tissue, the performance, accuracy and speed of the surgical procedure will be improved. Preferably use of the surgical devices of the present invention are useful for microsurgeries such as ophthalmologic and neurosurgical techniques.

The invention also includes methods for methods for use of devices of the invention, e.g. a method for treating a patient's eye, particularly in a vitreoretinal procedure or other eye or retina surgical procedure, comprising manipulating tissue of the patient with a device of the invention, wherein such manipulations are transmitted to a medical practitioner through the device in amplified form. Methods of the invention also include such use of a device of the invention in other microsurgeries such as nerurosurgery procedures and other endoscopic procedures.

The invention also includes device kits, which preferably comprise a device of the invention, preferably in packaged form, preferably packaged in sterile form optionally with an instruction sheet for use of the device.

Other aspects and embodiments of the invention are discussed infra.

DETAILED DESCRIPTION OF THE INVENTION

Referring now to the various figures of the drawing, wherein like references or characters refer to like parts, there is shown in FIGS. 1–14 various views and embodiments of a surgical devices in accordance with the present invention.

The surgical device will now be described below with reference to a surgical pick (see FIGS. 1–6). However, it is to be understood that the present invention is not limited to surgical picks, and that any other types of surgical instruments (e.g. probe, needle, cannula) are within the scope of the present invention.

The surgical device 800/900 in the form of a surgical pick includes a handle or hand piece 802/902, having a proximal end and a distal end, and a shaft 804/904 extending from the distal end of the handle 802/902. The shaft 804/904 has a proximal end and a distal end 808, see FIGS. 3–6. Surgical picks are well known and, thus, although described below with reference to a preferred embodiment, the general features (e.g. size, shape, materials) of the surgical pick may be in accordance with conventional surgical picks.

At the distal end 808 of the shaft 804/904 at the tip is a surgical pick 638. A sensor embedded in the shaft 804/904 determines any one (or more) of the physical properties of surgery. These properties include, but are not limited to, physical interactions between the surgical tool and the tissue (i.e. stress, strain, force, acceleration), electrical properties between the surgical tool and the tissue (i.e. impedance, magnetic flux) and spatial relations between the surgical tool and the tissue (i.e. contact, proximity). As the surgical pick is used during a procedure, the sensor 310 collects information based upon dynamic and/or static forces imposed upon the shaft 804/904 during the procedure. The information collected from the sensor 310 is processed and delivered to the medical practitioner in a non-visual manner. The sensor 310 used in the surgical device 800/900 of the present invention can be of any type known in the mechanical or electromechanical fields.

In a preferred embodiment (FIG. 5), the sensor 310 is a thin, plastic coated piezopolymer material embedded in the shaft 304/804/904. The piezopolymer may be attached by conventional fastening means such as, for example, adhesives or by a frictional fit. The piezopolymer generates an electric signal when dynamically flexed that is proportional to the degree of flexion.

Piezopolymer materials are well known in the art, as are mounting and electrical characteristics. Particular materials may be selected and adapted to suit the particular purpose of the device, such as for example, laminated or non-laminated materials. Preferred materials include metalized piezopolymer such as those supplies from Measurement Specialties, Inc.

In an additionally preferred embodiment the sensor is a thin, plastic coated piezoresistive material attached between the proximal end of the shaft and the handle. The piezoresistive material may be attached by conventional fastening means such as, for example, adhesives or by a frictional fit. The piezoresistive generates an electric signal when subjected to static pressures. Additionally, piezoresistive material has a reasonable dynamic response. The sensor changes resistance when a pressure is applied to it. By placing the sensor between the shaft of the instrument and the handle, it will act as a transmission between the handle and the shaft. In particularly preferred embodiments, the handle of the instrument should be rigid in order to maintain correct output voltage readings.

Piezoresistive materials are known to those of skill in the art, as are mounting and electrical characteristics. Particular materials may be selected and adapted to suit the particular purpose of the device, such as for example, laminated or non-laminated materials. Preferred materials may include for example, FlexiForce, (Tekscan), however any suitable piezoresistive material may be substituted.

Additionally preferred embodiments may include devices wherein the sensor element is comprised of strain gauges (see FIGS. 7–9) or fiber optic flexion sensors or other useful sensor materials (see FIG. 14) contained within or attached to the shaft of the device, wherein the sensors are capable of detection of dynamic and/or static forces applied to the device.

Selection of the particular material for sensor elements may be determined in part by the particular application of the device. For example, ophthalmic procedures may suffice with use of piezopolymer materials when primarily detection of dynamic forces is required. However, neuorsurgical devices may likely better suited through use of piezoresistive materials or strain gauges, in order to convey not only dynamic forces such as texture and impact, but also static forces such as force of retraction.

The tactile pick is a modification of existing surgical instruments and is used in exactly the same manner. As such, there is no risk to the patient as a result of the shape of the instrument or the intended use. The sensor and sensor electronics present an additional risk to the patient not present in existing picks, however, the electronics have been designed to completely insulate and isolate the patient from the circuitry. The sensor 310 itself is embedded within the shaft 304 of the instrument and is completely encased in silicone filled polyimide tubing 312 (see FIG. 5). There is no conductive path from the pick to the sensor and therefore no conductive path from the patient to the sensor. As an additional safety precaution, the sensor amplification electronics are powered from an isolation transformer that completely separates the circuit from earth ground.

Figure 1:
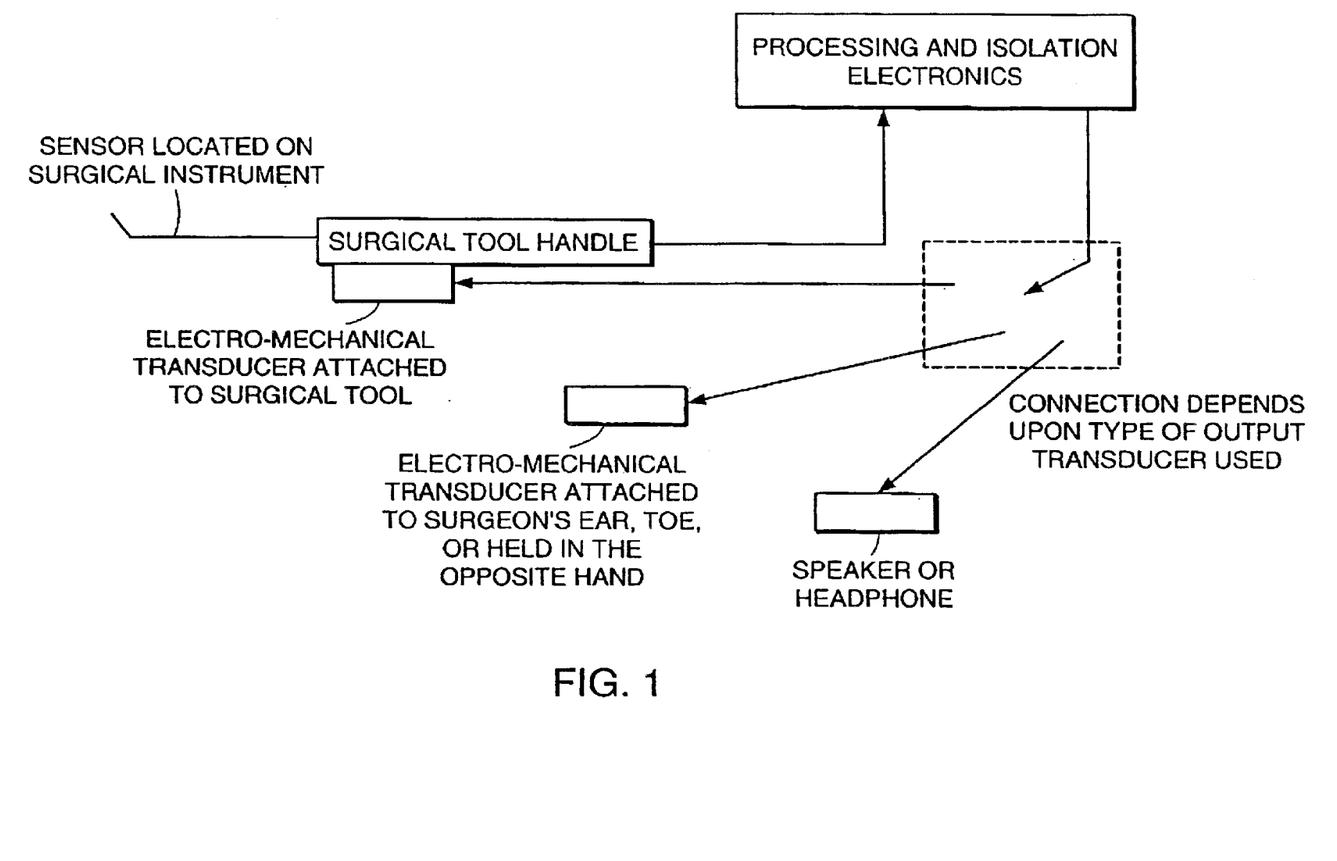
FIG. 1 is a schematic block diagram depicting the surgical tool, electronics and connections involved in operation of the device.
Figure 2:
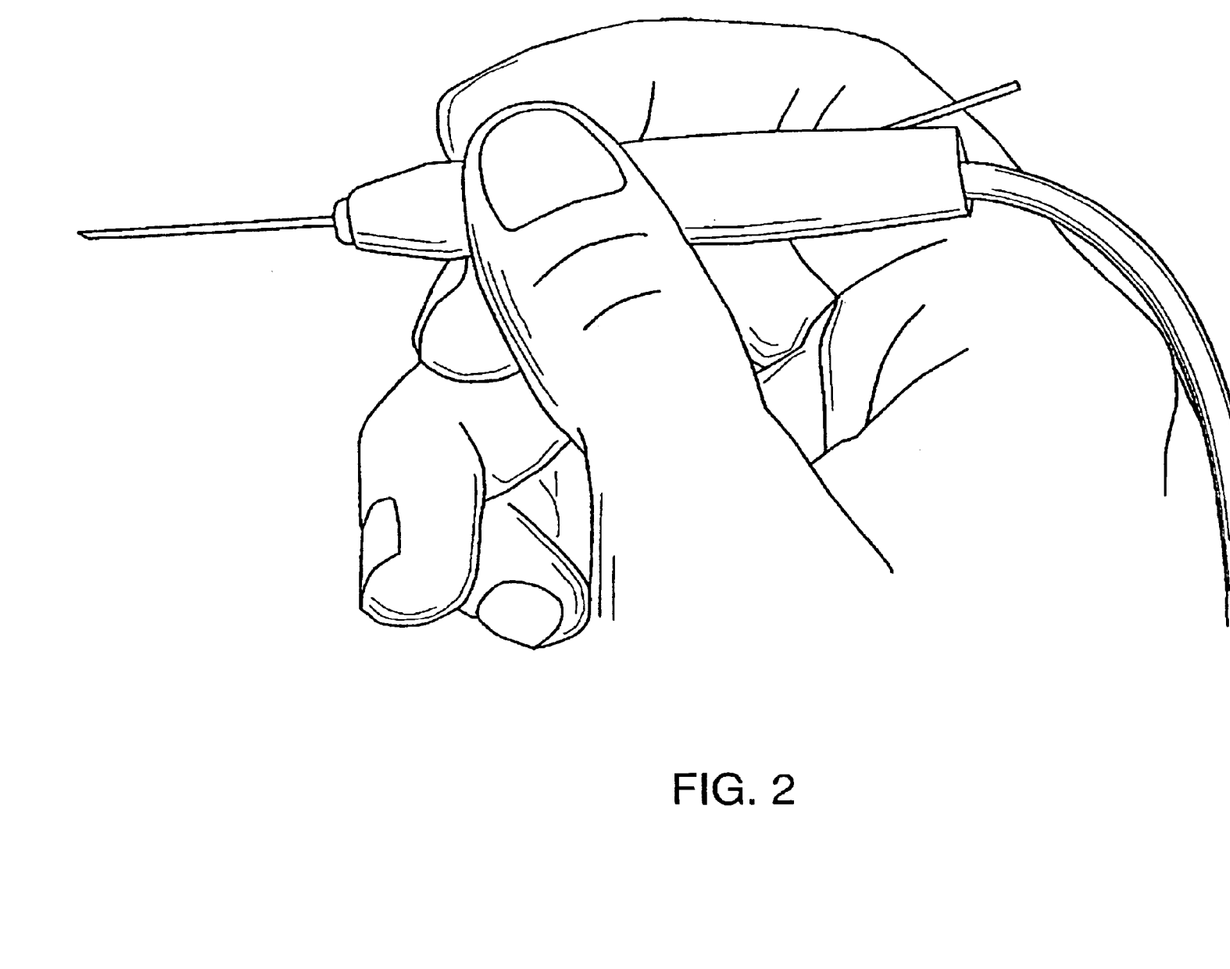
FIG. 2 shows one embodiment of the surgical device with enhanced perception in accordance with the present invention utilizing piezopolymer sensor elements.
Figures 3, 4, 5, 6:
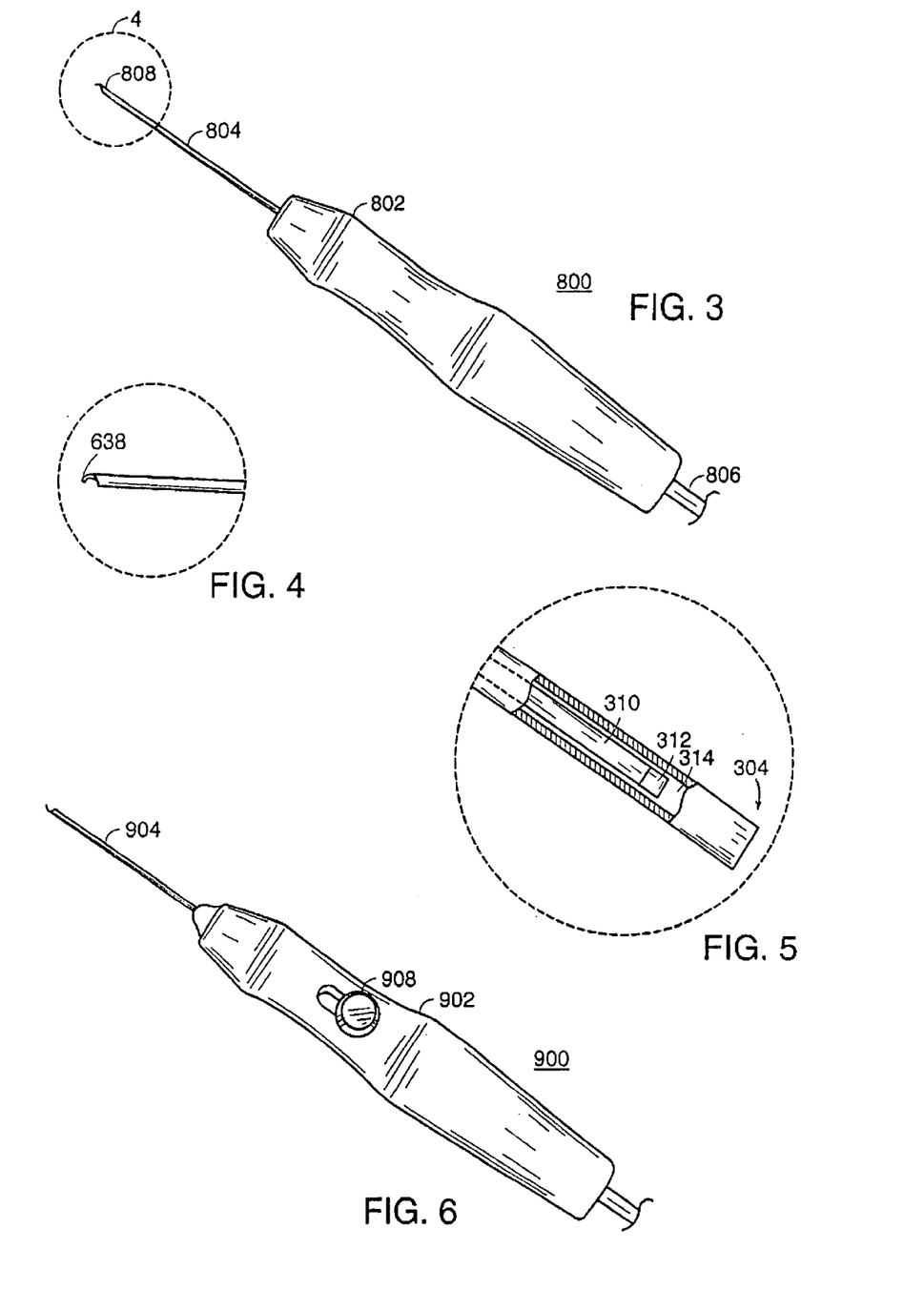
FIG. 3 is a schematic diagram depicting one embodiment of the surgical device with enhanced perception utilizing piezopolymer sensor elements.
FIG. 4 is a schematic diagram depicting a close-up of a surgical pick.
FIG. 5 is a schematic diagram depicting a cut-away view demonstrating the sensor element construction of one embodiment of the surgical device with enhanced perception utilizing piezopolymer sensor elements.
FIG. 6 is a schematic diagram depicting one embodiment of the surgical device with enhanced perception having an output transducer on the handle.
Figure 7:
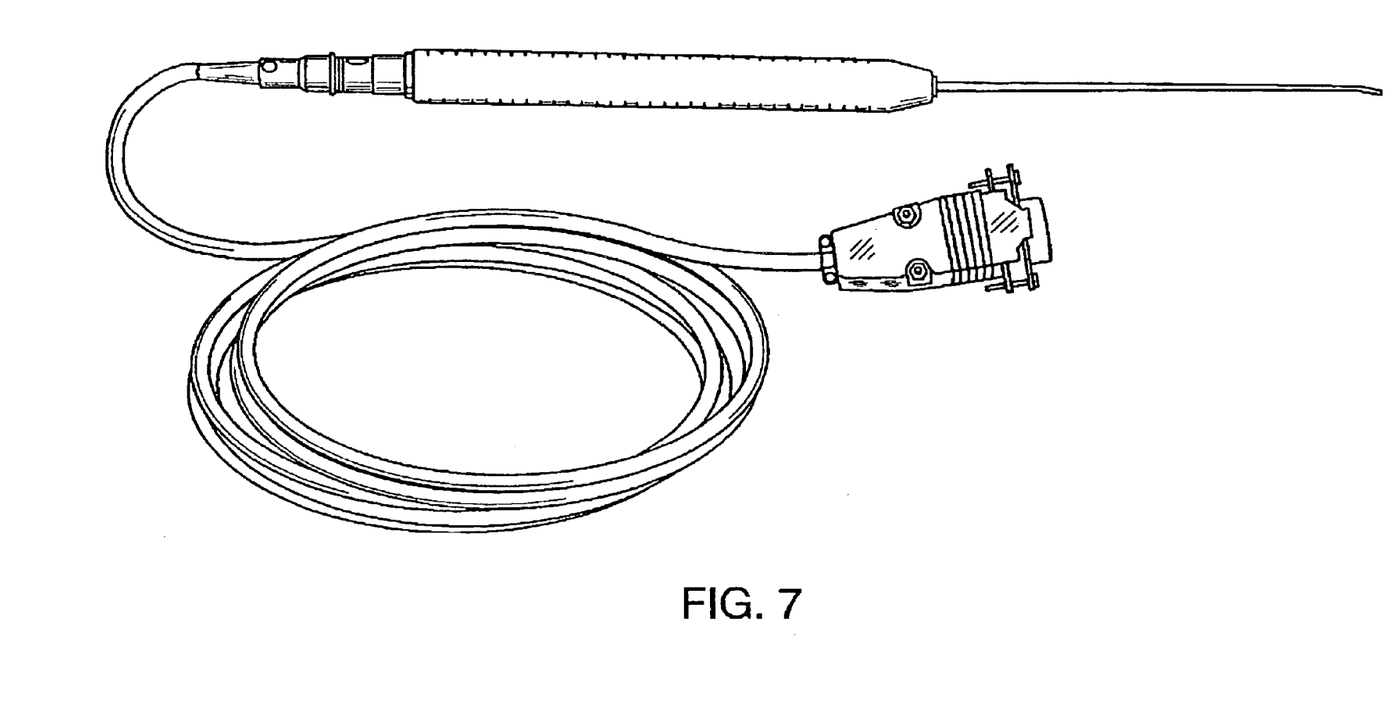
FIG. 7 shows one embodiment of the surgical device with enhanced perception in accordance with the present invention utilizing strain gauge sensors.

Signal produced from the sensor element 310 may then be filtered, conditioned, and amplified by, for example, an isolation amplifier and then used to drive any one of several output devices. For example, as shown in FIG. 1, the signal produced from the sensor element 310 passes to processing and isolation electronics 106 to the output device 100, which may be an electromechanical transducer 102 attached to the handle of the surgical device or attached to the medical practitioner, a speaker or headphone 104 or a combination of these output devices.

In one embodiment, an output device 100 is an electromechanical transducer in the form of a small speaker glued inversely to the handle such that output in the speaker causes the cone of the speaker to remain stationary while the body of speaker moves against the medical practitioner's hand. In another embodiment, the medical practitioner holds the surgical pick in one hand, while holding, for example, a speaker, in his other hand.

In a preferred embodiment, the surgical pick is constructed out of standard shim stock, such as stainless steel for example, the thickness of which can be selected based on the degree of sensitivity required. A thin, plastic coated piezopolymer sensor 310, was placed within the shaft 304 of the custom fabricated pick, see FIG. 5. For electrical isolation, the piezopolymer strip may be epoxied within a polyimide tube 312, then the pick and the encapsulated sensor housed in an additional polyimide sheath 314 and filled with silicone rubber. The piezopolymer generates an electric signal when dynamically flexed that is proportional to the degree of flexion of the pick portion 638. The piezopolymer may, if desired, be trimmed down to form the shape of a conventional surgical pick. Electronic leads may be attached to or located on the piezopolymer, then may be run through the handle and connected to an external electronic controller such as an amplifier electronics box. For example, the signal may be conditioned using a 60 Hz notch filter and an isolation amplifier.

Preferably the output of the amplifier may then be used to drive any one of several output devices, including, for example, a small speaker glued inversely to the handle (cone is stationary, body of speaker moves), a speaker held in the opposite hand of the medical practitioner, an amplified computer speaker, or a speaker mounted to the medical practitioner's footpedal controller. In one embodiment a speaker such as, a small 8 ohm speaker or an amplified computer speaker may be used as a signal generator. The may be suitably attached to the instrument handle or held by the medical practitioner. The speaker vibrates in response to the pick contacting tissue, resulting in an auditory representation of tactile and haptic information normally too small to be perceived by the medical practitioner.

Figure 8:
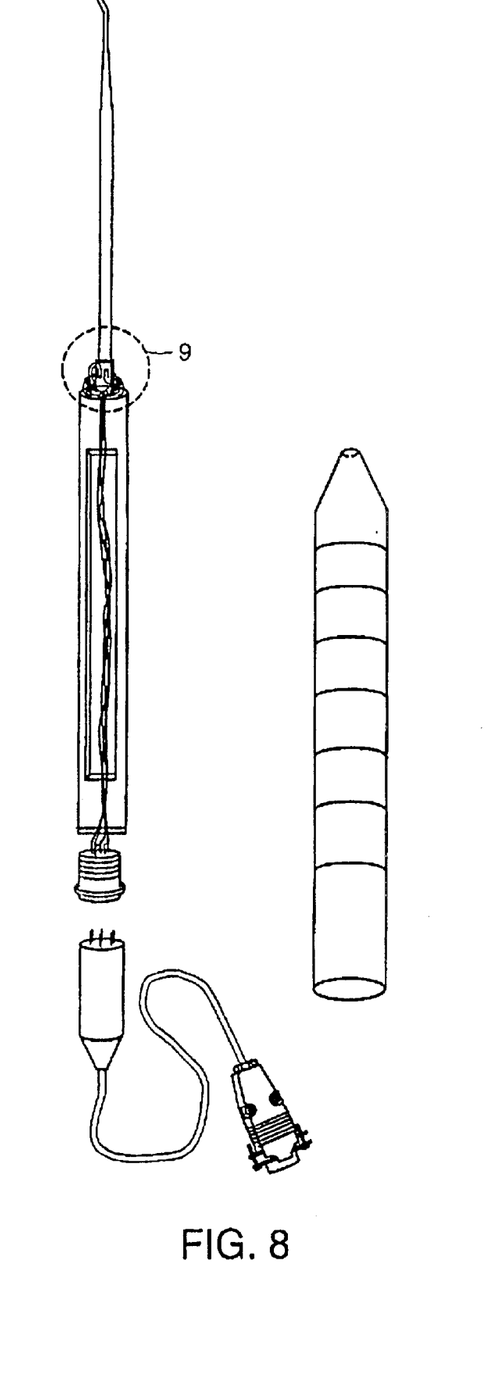
FIG. 8 is a schematic diagram depicting one embodiment of the surgical device with enhanced perception utilizing strain gauge sensors.
Figure 9:
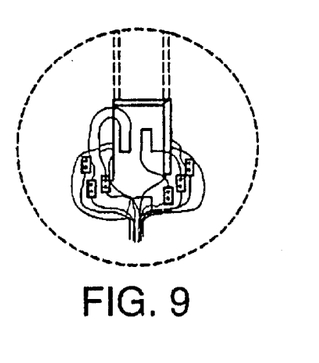
FIG. 9 is a schematic diagram depicting a cut-away view demonstrating the sensor element construction of one embodiment of the surgical device with enhanced perception utilizing strain gauge sensors.

FIGS. 8 and 9 show detailed views of one exemplary embodiment of the surgical device in accordance with the invention. One or more wires 810 may extend through the length of the shaft 804/904 and to the proximal end of the device where they are wired to a connector 812. Strain gages, shown in detail in FIG. 9 may be mounted on the shaft 804/904, preferably on each side of the shaft 804/904, as shown. In a preferred embodiment, four total fill-bridge configuration strain gages are mounted on each side of the shaft 804/904 and then soldered onto solder tabs. In one embodiment, the surgical pick 638 is tear shaped, as shown in FIG. 8, and is approximately 0.035 inch at its thickest point. The surgical pick 638 preferably extends at an angle θ from the distal end 808 of the shaft 804/904. On one embodiment, the surgical pick 938 is approximately 0.3 inch in length. In the embodiment shown in FIG. 8, the shaft 804/904 tapers towards its distal end 808. For example, in one embodiment, the shaft 804/904 may have a thickness of approximately 0.055 inch at its thickest portion and a thickness of approximately 0.025 inch at its narrowest portion. In some embodiments the length of the shaft 804/904 from its proximal end to the point at which it begins to taper is at least 10 times as long as the length of the remaindering tapered portion. In one embodiment, for example, the length of the thickest portion of the shaft 804/904 is approximately 4.46 inch and length of the tapered portion of the shaft is approximately 0.313 inch. In the embodiment shown in FIG. 8, the wires 810 run through the length of the shaft 904/904, through the strain gages, and to the connector 812. In one embodiment, the strain gages are nearly four inches away from the connector 810, preferably 3.9 inch. A handle 802/902 is mounted to preferably cover the strain gages and all electrical connections. In an exemplary embodiment, the handle 802/902 has an overall length of approximately five inches. The handle 802/902 is hollow and preferably had a wall thickness of approximately 0.1 inch. For example, in one embodiment, the handle has an inner diameter of approximately 0.4 inch and an outer diameter of approximately 0.5 inch. The handle 802/902 is shown to taper towards its distal end. In one exemplary embodiment, the length of the handle 802/902 from its proximal end to the point where the handle begins to taper is approximately 4.645 inch and the tapered portion tapers to an inner diameter of approximately 0.2 inch and an outer diameter of approximately 0.3 inch. Of course, these dimensions may vary and depend on the type of device used and the application of the device m use. For example, when the device is used in larger surgical areas, the device may be larger. On the other hand, when the device is used in smaller surgical areas, for example, during arthroscopic procedures, the device may be smaller. Further, the dimensions of the handle, shaft, surgical pick and other portions of the device vary relative to each other. For example, the handle 802/902 is mounted to preferably cover the strain gages and all electrical connections. Thus, the handle 802/902 is sized accordingly.

Figure 10:
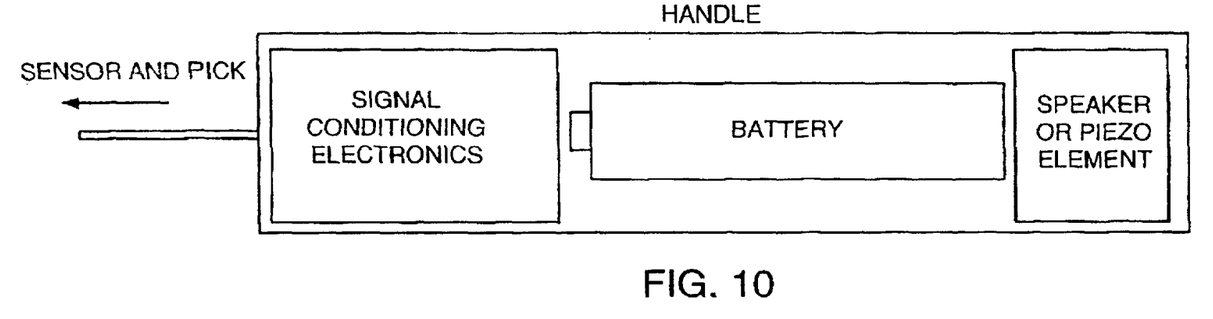
FIG. 10 is a schematic block diagram demonstrating a self-contained embodiment of the surgical device with enhanced perception.

In a particularly preferred embodiment, the surgical device, as shown in FIG. 10, is self contained and battery operated. Preferably, the handle is hollow and contains signal conditioning electronics 108, one or more batteries 110 and an electromechanical transducer 102.

Figure 11:
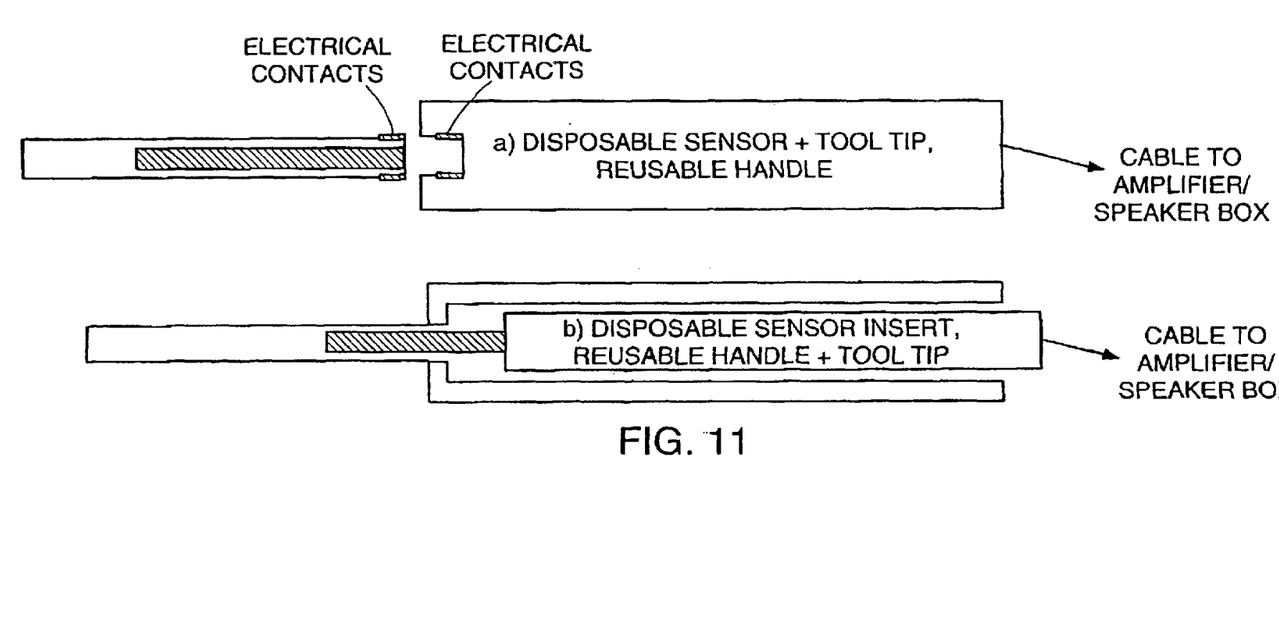
FIG. 11 is schematic block diagrams demonstrating disposable/reusable embodiments of the surgical device with enhanced perception.
Figure 12:
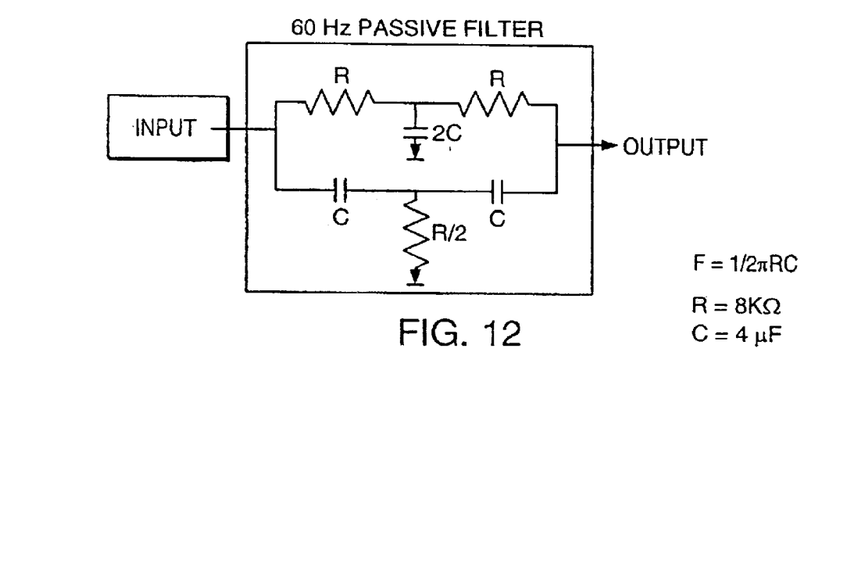
FIG. 12 is a circuit diagram depicting electronic amplifier and filter of the electronic controller of a surgical device with enhanced perception.
Figure 13:
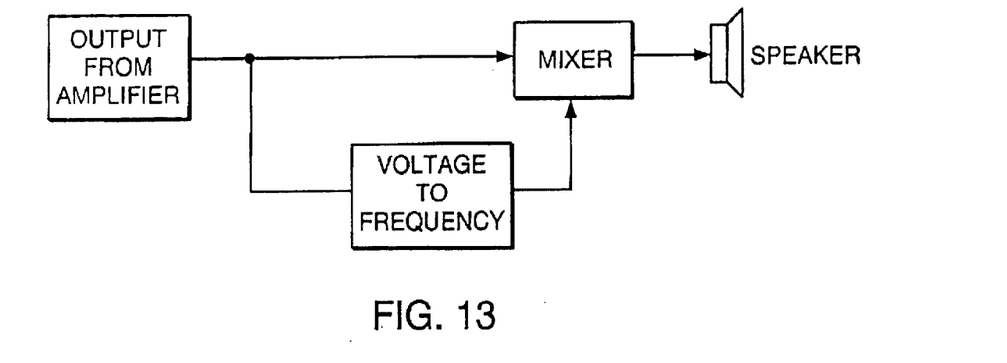
FIG. 13 is a schematic block diagram depicting output of mixed signals generated from static and dynamic forces.
Figure 14:
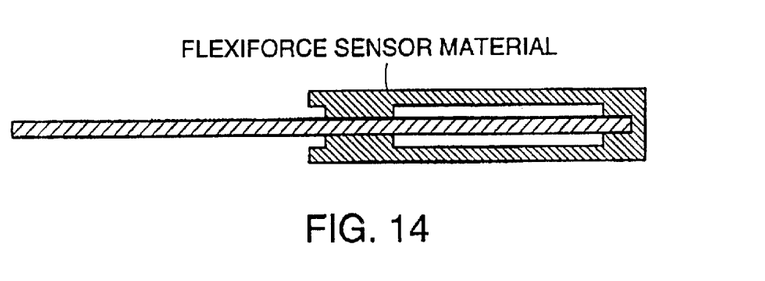
FIG. 14 is a schematic block diagram depicting one embodiment of the surgical device with enhanced perception utilizing FlexiForce sensor material.

An additional preferred embodiment includes a surgical device comprised of modular elements, some of which may be disposable and/or reusable. For example, a disposable instrument tip 112 containing the sensor 310 or a disposable insert as shown in FIG. 11 may be used. Such disposable instruments may be used in conjunction with a reusable instrument having an electrical cable connecting the surgical instrument to an external box containing the processing electronics.

A surgeon may use a tactile pick in the same manner whether the perception enhancement electronics are on or off. During the surgical procedure, the tactile pick may be used without the amplifying electronics enabled. During the procedure, the electronics may be enabled, allowing microforces present at the tip of the instrument to be picked up by the sensor, amplified and sent to the surgeon via tactile or auditory means. This will, therefore, expand microsurgery from a purely visual art to one with multimodal sensory input.

The sensor element is embedded within the shaft of the surgical instrument and is completely isolated from the patient. Amplifying electronics are similarly isolated from the patient and separated from ground through the use of an isolation transformer. This instrument will provide auditory information to the medical practitioner about such information as when the tool tip contacts tissue and with how much force. It will also inform the medical practitioner as to what force the tissue is being pushed or pulled during manipulation. This information is currently unavailable to the medical practitioner and must be assumed indirectly by visual observation of the tissue through a microscope.

The sensor produces a differential voltage when bent. The leads of the sensor are connected to a signal conditioning box through a shielded two-conductor cable. The box amplifies the signal (×500) using an instrumentation amplifier with jumper selectable gain and then filtered the signal through a 60 Hz passive notch filter. The output of the filter is suitable for driving a standard audio amplifier as found in powered external computer speakers, however any differential amplifier may be used. See FIG. 12.

It is preferable to vary the vibrational intensity of the output elements relative to the force sensed in such away that the medical practitioner perceives a doubling of the sensation when a doubling of the force imparted upon the device arises.

In one embodiment, a plurality of output elements, such as electromechanical transducers including tactile actuators or audio equipment capable of producing signals representative of tactile parameters may be used to generate a plurality of audible and/or tactile signals in conjunction with output of the device. See FIG. 1.

The actuators used in the device according to the invention can be any means known in the mechanical or electromechanical fields and more particularly those utilized in the implementation of known handling devices. In particular elements of the moving core solenoid type, capable of exerting forces and of moving the articulated elements of the operating hand can be used, and for the slave hand electric motor controls can be used, associated with a system of rods, permitting the adjustment of the mechanical parameters to be produced as a function of the electrical parameters of the motors. The actuator system can be included within the hand-piece of the instrument in the way of miniature stepping motors, servo motors, linear magnetic actuators, or others. As actuators capable of producing tactile sensations, devices producing the parameter detected (electric signal, for example) can be used or even devices applying a signal representative of this parameter (for example an electrical impulse of which the amplitude or the frequency is a function of the value of the detected pressure).

In an additional embodiment, the instant invention employs a microprocessor control element which is coupled to the electronic controller assembly of the surgical device. The output signal from sensor is carried through cable to electronic controller which has its output connected to an output transducer means for audibly or tactically reproducing the output of the sensor for operator perception. Coupling of the microprocessor control element to the electronic controller assembly thus provides means for adjusting the sensitivity and threshold levels of the electronic controller, resulting in adjustment of the increased perception of the medical practitioner utilizing the device.

The device may take the output from the electronic controller or amplifier box and directly drive a speaker 100/104. This works fine for a dynamic signal, however for static forces, no "sound" would be generated when the sensor is flexed and then held. Thus, for measurement of static forces, preferably the electronic controller mixes the output from the amplifier with the output from the amplifier after it is run through a frequency to voltage converter. See FIG. 13. The FVC will take the DC portion of the output signal and convert it into a tone. The pitch will vary as the sensor is pressed harder, thus resulting in frequency as an indicator the applied force. Thus, mixing signal with the dynamic output, the medical practitioner will be able to perceive both static and dynamic forces.

The foregoing description of the invention is merely illustrative thereof, and it is understood that variations and modifications can be effected without departing from the scope or spirit of the invention as set forth in the following claims.

What is claimed is:

1. A surgical device comprising:
   a sensor element for detecting dynamic and static forces imparted on the device, wherein non-visual information relating to these forces is communicated to a user of the device and the sensor element is capable of detecting a spatial relation of the device with the environment.

2. The device of claim 1 wherein information relating to forces imparted on the device is amplified and then communicated to the user.

3. The device of claim 1 wherein the non-visual information is tactile or auditory.

4. The device of claim 1 wherein the sensor element transmits an electrical signal in response to forces imparted on the device.

5. The device of claim 1 wherein the sensor element generates electrical signals based on forces imparted at a distal end of the device.

6. The device of claim 1 wherein the device is adapted for a microsurgery procedure.

7. The device of claim 1 wherein the device is adapted for an ophthalmic procedure.

8. The device of claim 1 wherein the device is adapted for neurosurgery.

9. The device of claim 1 wherein the device comprises a sensor element for sensing forces imparted along a substantial length of the device.

10. The device of claim 1 wherein the sensor element generates a proportional signal in response to a force on the device, wherein the strength of the signal is proportional to the amount of force on the device.

11. The device of claim 10 wherein the device further comprises an electronic controller for generating an output signal based on the proportional electrical signal.

12. The device of claim 11 wherein the device further comprises an output transducer for receiving the output signal, wherein the output transducer produces a sensory signal proportional to the amount of force imparted on the device.

13. The device of claim 12 further comprising an energy conducting apparatus for transmitting the output signal from the electronic controller to the output transducer.

14. The device of claim 12 wherein the output transducer is any one of a speaker, earphone or headphone.

15. The device of claim 1 wherein the output transducer is an electromechanical transducer.

16. The device of claim 15 wherein the electromechanical transducer is attached to a grip portion of the device.

17. The device of claim 15 wherein the electromechanical transducer is attached to a medical practitioner that uses the device.

18. The device of claim 1 further comprising a mechanism that transmits electric signals from the sensor element to the electronic controller.

19. The device of claim 1 further comprising a power source for the device.

20. The device of claim 19 wherein the power source is connected to the device through an electrical cable.

21. The device of claim 1 wherein the device comprises a battery.

22. The device of claim 7 wherein the sensor element comprises a piezopolymer.

23. The device of claim 22 wherein the piezopolymer generates an electric signal when flexed that is proportional to the degree of flexion.

24. The device of claim 1, wherein the device includes a shaft and the sensor element comprises a strain gauge contained within, or attached to, the shaft.

25. The device of claim 9 wherein the electronic controller operates under control of a microprocessor.

26. The device of claim 25 wherein the microprocessor provides an ability to adjust the sensitivity and threshold of operation of the device.

27. The device of claim 1 wherein the surgical device is self-contained.

28. The device of claim 1 wherein the device is adapted to be sterilized.

29. The device of claim 1 wherein one or more parts of the device are modular.

30. The device of claim 29 wherein the one or more parts are disposable.

31. The device of claim 29 wherein the one or more parts are reuseable.

32. The device of claim 1 wherein the device interacts with an environment and senses impedance or magnetic flux in the environment.

33. The device of claim 1 wherein the device senses proximity and/or contact with a tissue.

34. The device of claim 1 wherein the device comprises a shaft having a distal end and a handle and wherein the sensor is placed between the shaft and the handle.

35. The device of claim 34 wherein the handle is rigid.

36. The device of claim 1 wherein the device comprises a shaft and the sensor is imbedded within the shaft.

37. The device of claim 1 wherein the device comprises a disposable tip.

38. A method of performing a medical procedure, comprising bringing a device according to claim 1 into proximity with a tissue and sensing static and/or dynamic forces on the device.

39. The method of claim 38 further comprising the step of guiding the device based on non-visual information received in response to the sensing.

40. The method of claim 38 or 39 further comprising manipulating the tissue of a patient with the device.

41. The method of claim 38 wherein the tissue is neurological tissue.

42. The method of claim 38 wherein the tissue of a patient's eye is manipulated.

43. The method of claim 38 wherein the medical procedure is a surgical procedure.

44. The method of claim 38 or 39 wherein non-visual information is transmitted in real time to a user of the device.

45. The method of claim 38 wherein non-visual information which is tactile and/or auditory is transmitted to a user of the device.

46. The method of claim 38 where signals corresponding to forces on the device are amplified and communicated to a device user.

47. The method of claim 46 wherein the signals are electrical signals.

48. A kit comprising a device of claim 1 packaged in a sterile form.

* * * * *